(12) United States Patent
Luo et al.

(10) Patent No.: US 9,273,407 B2
(45) Date of Patent: Mar. 1, 2016

(54) ADDITIVE FOR ELECTRODEPOSITION

(71) Applicant: Hong Kong Applied Science and Technology Research Institute Co. Ltd., Shatin, New Territories (HK)

(72) Inventors: Jiye Luo, Hong Kong (HK); Yaofeng Sun, Hong Kong (HK); Shu Kin Yau, Hong Kong (HK)

(73) Assignee: Hong Kong Applied Science and Technology Research Institute Company Limited, Hong Kong (CN)

( * ) Notice: Subject to any disclaimer, the term of this patent is extended or adjusted under 35 U.S.C. 154(b) by 0 days.

(21) Appl. No.: 14/215,092

(22) Filed: Mar. 17, 2014

(65) Prior Publication Data

US 2015/0259814 A1 Sep. 17, 2015

(51) Int. Cl.
| | |
|---|---|
| *C07C 217/28* | (2006.01) |
| *C25D 3/38* | (2006.01) |
| *C07D 207/06* | (2006.01) |
| *C07D 211/14* | (2006.01) |

(52) U.S. Cl.
CPC ................ *C25D 3/38* (2013.01); *C07C 217/28* (2013.01); *C07D 207/06* (2013.01); *C07D 211/14* (2013.01)

(58) Field of Classification Search
None
See application file for complete search history.

(56) References Cited

U.S. PATENT DOCUMENTS

| | | |
|---|---|---|
| 4,110,176 A | 8/1978 | Creutz |
| 5,348,578 A | 9/1994 | Le Disert |
| 7,510,639 B2 | 3/2009 | Wang et al. |
| 7,662,981 B2 | 2/2010 | Wang et al. |
| 8,454,815 B2 | 6/2013 | Niazimbetova et al. |
| 2008/0087549 A1 | 4/2008 | Ishizuka et al. |
| 2011/0290660 A1 | 12/2011 | Niazimbetova et al. |
| 2013/0043137 A1 | 2/2013 | Yasuda et al. |

FOREIGN PATENT DOCUMENTS

| | | |
|---|---|---|
| CN | 1908240 A | 2/2007 |
| CN | 102276796 A | 12/2011 |
| EP | 1201789 A2 | 5/2002 |
| TW | 201136891 | 11/2011 |

OTHER PUBLICATIONS

First office action of CN201410119878.7 (cover), Mar. 16, 2015.
Text of the First office action of CN201410119878.7, Mar. 4, 2015.
Synthesis and Properties of Multiarmed Geminis. Frederic M. Menger and Vasily A. Migulin. 1999, J. Org. Chem., Issue 64, vol. 64, p. 8916-8921.
Structural Characteristics of Low-molecular-mass displacers for cation-exchange chromatography II. Role of the stationary phase. Aabhinav A. Shulka, S. Bae, J. A. Moore. Steven M. Cramer. 1998, Journal of Chromatography A, Issue 827, vol. 2, pp. 295-310.
RN: 790643-86-6, 788808-99-1, 771462-52-3, 747396-74-3, 738596-11-7, 252644-10-3, 252644-09-0, 252644-08-9, 221119-14-8, 213251-85-5, 376393-96-3. Chemical Abstract Service, CA online version STN Registry database. Last updated Nov. 30, 2004.

*Primary Examiner* — Clinton Brooks
*Assistant Examiner* — Jennifer C Sawyer
(74) *Attorney, Agent, or Firm* — Eagle IP Limited; Jacqueline C. Lui

(57) ABSTRACT

This invention relates to a new compound represented by formula (I). Particularly, the new compound is used as an additive in copper electroplating. A chemical structure for the leveler, an electroplating bath containing the same, a method of preparing the additive and a method of electroplating a substrate with the electroplating bath containing the additive are disclosed. The additive compound/molecule of the present invention provides a branched structure at each ends, wherein each of the branches comprises a positively charged nitrogen moiety. The additive compound/molecule is formed by linking the branches having the positive charged nitrogen moieties to the backbone of the additive compound/molecule. This leads to a high charge density novel additive compound/molecule.

13 Claims, 4 Drawing Sheets

ADDITIVE FOR ELECTRODEPOSITION

FIELD OF INVENTION

This invention relates to a new compound, particularly, this new compound can be used as an additive for electroplating.

BACKGROUND OF INVENTION

During electroplating, a voltage drop variation typically exists along an irregular surface of a substrate which can result in an uneven metal deposit on the substrate. Some parts of the substrate would have been overplated while other parts would have been underplated. This would particularly be a problem when there is a hole on the surface of the substrate. For example, FIG. 1 shows a scanning electron micrograph ("SEM") of a hole 20 on a substrate having copper 22 electroplated on it by a conventional electroplating process (i.e. electroplating a substrate by submerging it into an electroplating bath without any additives). As shown in FIG. 1, the edge of the hole 20 is overplated with copper 22, while the inner walls of the hole 20 are underplated. As a result, the inner volume of the hole 20 is not properly filled and the resulting conductivity of the substrate plated with copper 22 would be greatly affected.

Levelers have been added into the electroplating bath in order to achieve a uniform metal deposit on a substrate surface. Although the conventional levelers improve the quality of metal deposit done by electroplating on the substrate surface, the quality is still not as desired.

SUMMARY OF INVENTION

In the light of the foregoing background, it is an object of the present invention to provide a new and alternate additive, particularly, an alternate leveler for copper electroplating.

Accordingly, the present invention, in one aspect, is a compound represented by the following formula (I)

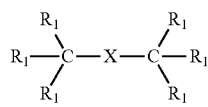
(I)

wherein X represents a linker group comprising a backbone which further comprises a predetermined number of carbon atoms, in which at least one of the carbon atoms is optionally substituted by oxygen atom and/or nitrogen atom and/or sulfur atom; and $R_1$ represents a positively charged functional group comprising a plurality of carbon atoms and at least one positively charged nitrogen moiety.

In one embodiment, wherein $R_1$ is further represented by the following formula (II)

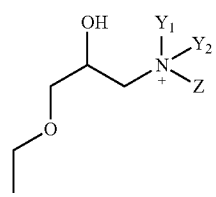
(II)

wherein $Y_1$ and $Y_2$ respectively represents a first and second chained group, where each of the chained group comprises a backbone comprising a predetermined number of carbon atoms, wherein at least one of the carbon atoms is optionally substituted by oxygen atoms and/or nitrogen atoms and/or sulfur atoms; and Z represents a hydrogen or a hydrocarbon of $C_1$-$C_{20}$ optionally having unsaturated bonds or hydroxyl groups.

According to another aspect of the present invention a method of electroplating a substrate comprising the steps of
a) contacting the substrate with an electroplating bath comprising a compound represented by formula (I); and
b) applying an electric current to the substrate for a predetermined period of time such that a plating is formed on the substrate, wherein X represents a linker group comprising a backbone which further comprises a predetermined number of carbon atoms, in which at least one of the carbon atoms is optionally substituted by oxygen atom and/or nitrogen atom and/or sulfur atom; and $R_1$ represents a positively charged functional group comprising a plurality of carbon atoms and at least one positively charged nitrogen moiety.

In a further aspect of the present invention, a method of a process for preparing a leveler for the use in electroplating comprising the step of contacting an amine with an epoxide-containing reagent represented by the following formula (XX)

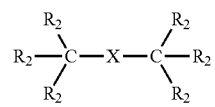
(XX)

wherein X represents a linker group comprising a backbone which further comprises a predetermined number of carbon atoms, in which at least one of the carbon atoms is optionally substituted by oxygen atom and/or nitrogen atom and/or sulfur atom; and $R_2$ represents another chained group comprising at least one epoxide functional group.

In one embodiment, the method of a process for preparing a leveler for the use in electroplating further comprises the step of adding a halogen-containing reagent represented by the following formula (XXIV)

(XXIV)

wherein V represents a halogen; and Z represents a group consisting of a hydrogen, a hydrocarbon of $C_1$-$C_{20}$ optionally having at least one unsaturated bond and/or hydroxyl group.

There are many advantages to the present invention. Firstly, the additive of the present invention provides a branched structure at each end of the additive compound/molecule, wherein each of the branches comprises a positively charged nitrogen moiety. The additive compound/molecule is formed by linking the branches having the positively charged nitrogen moieties to the backbone of the additive compound/molecule. This leads to a novel additive compound/molecule with high charge density, in which there are at least 6 positive charges within a single additive compound/molecule of the present invention.

Another advantage of the present invention is that the ratio of nitrogen and oxygen in the additive compound/molecule of the present invention is adjustable according to the practical needs. Thus, the additive compound/molecule of the present invention can be used in more versatile applications than the conventional levelers, which have fixed nitrogen to oxygen ratio.

Further, in 3D-IC integration, which is the future of microelectronics, one of the key technologies is 3D vertical interconnects, including nanometer damascene trench, microbumps for flip chip assembly, TSV for chip stacking, and microvias in multilayer substrate. The fabrication of those interconnects by copper electrochemical deposition is a challenging process. As the microvia size continues decreasing for electronics miniaturization, thinner surface plating thickness and smaller dimple depth are required. A further advantage of the present invention is that the additive molecule/compound of the present invention can be used as a leveler in conjunction with accelerator and suppressor to provide a high filling power in copper electrochemical deposition. Therefore, high quality plating with thin surface plating thickness and substantially no dimple after electrochemical deposition can be achieved.

DETAILED DESCRIPTION OF THE PREFERRED EMBODIMENTS

Figure 1:
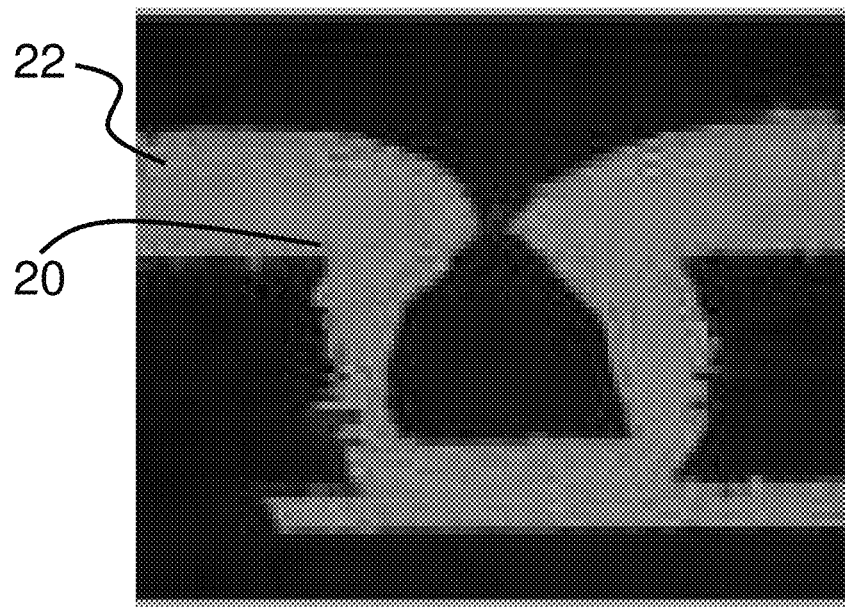
FIG. 1 shows a scanning electron micrograph ("SEM") of a hole on a substrate having copper electroplated on it by a conventional electroplating process from a prior art document.

As used herein and in the claims, "comprising" means including the following elements but not excluding others.

The present invention provides an additive compound/molecule which can be used in electroplating. Particularly, the additive compound/molecule can be used as a leveler for copper electroplating. The additive compound/molecule comprising, as an effective ingredient, represented by the following general formula (I)

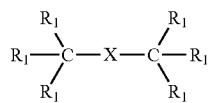

(I)

wherein X represents a linker group comprising a backbone which further comprises a predetermined number of carbon atoms, in which at least one of the carbon atoms is optionally substituted by oxygen atom and/or nitrogen atom and/or sulfur atom; and $R_1$ represents a positively charged functional group comprising a plurality of carbon atoms and at least one positively charged nitrogen moiety.

Now referring to the positively charged functional group $R_1$. The following formula (II) represents a general formula of the positively charged functional group $R_1$

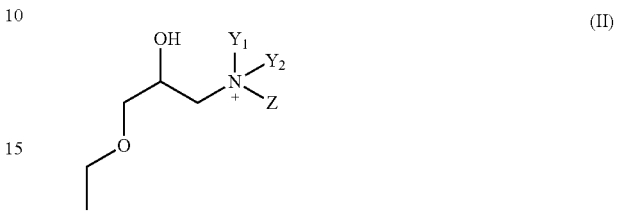

(II)

wherein $Y_1$ and $Y_2$ respectively represents a first and second chained group, where each of the chained group comprises a backbone which further comprises a predetermined number of carbon atoms, wherein at least one of the carbon atoms is optionally substituted by oxygen atoms and/or nitrogen atoms and/or sulfur atoms; and Z represents a hydrogen or a hydrocarbon of C1-C20 optionally having unsaturated bonds or hydroxyl groups.

In one embodiment, the predetermined number of carbon atoms in each of the backbone of the first and second chained groups ($Y_1$ and $Y_2$) is in a range of 1 and 20. In another embodiment, the backbones of $Y_1$ and $Y_2$ jointly form a cycloalkyl group of $C_3$-$C_8$.

Further, in another specific embodiments, the positively charged functional group $R_1$ can be represented by the following formulas (III)-(V)

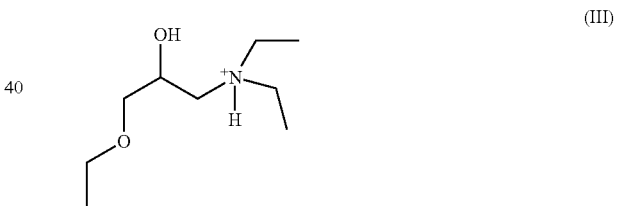

(III)

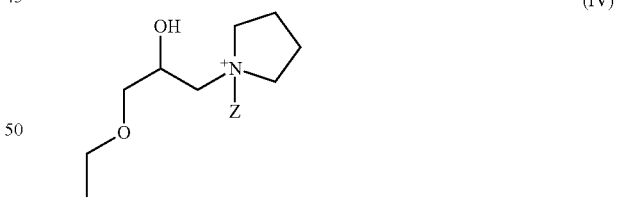

(IV)

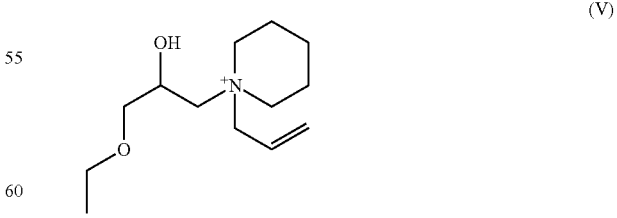

(V)

wherein Z represents a hydrogen or a hydrocarbon of $C_1$-$C_{20}$ optionally having at least one unsaturated bond or hydroxyl group.

Now referring to the linker group X. In one embodiment, the number of carbon atoms in the backbone of the linker group is in a range of 1 and about 100, wherein the backbone optionally comprises at least one unsaturated bond. In another embodiment, the unsaturated bond can be a double bond or a triple bond formed between two carbon atoms. In one specific embodiment, the linker group X is selected from a group consisting of the following general formulas (VI)-(IX):

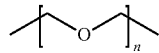
(VI)

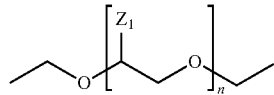
(VII)

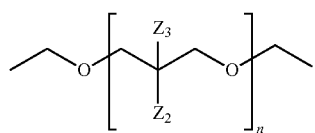
(VIII)

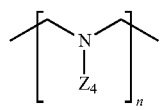
(IX)

wherein n is in the range of 1 and 50; $Z_1$ represents a hydrogen or hydrocarbon of $C_1$-$C_{20}$ optionally having at least one unsaturated bond; $Z_2$ represents a hydroxyl group or $R_1$; $Z_3$ represents a hydrogen or $R_1$; and $Z_4$ represents a hydrogen or a hydrocarbon of $C_1$-$C_{20}$ optionally having unsaturated bonds or hydroxyl groups.

Particularly, the specific embodiment of the linker group X that falls under the general formula (VI) is represented in the following formula (VI)(i)

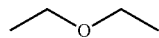
(VI)(i)

The specific embodiments of the linker group X that fall under the general formula (VII) are represented in the following formulas (VII)(i)-(VII)(iii)

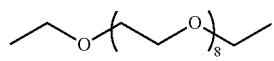
(VII)(i)

(VII)(ii)

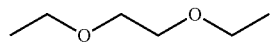
(VII)(iii)

The specific embodiments of the linker group X that falls under the general formula (VIII) are represented in the following formulas (VIII)(i) and (VIII)(ii)

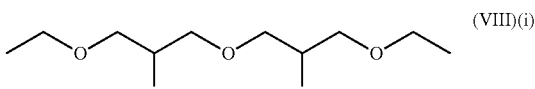
(VIII)(i)

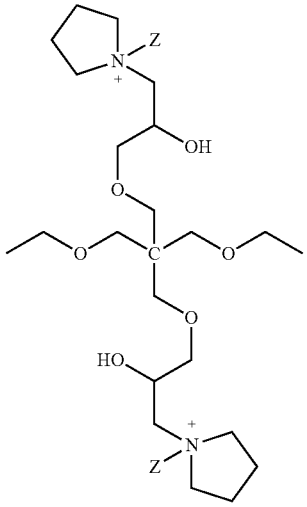
(VIII)(ii)

wherein Z represents a hydrogen or a hydrocarbon of $C_1$-$C_{20}$ optionally having unsaturated bonds or hydroxyl groups.

The specific embodiments of the linker group X that fall under the general formula (IX) are represented in the following formulas (DOW and (IX)(ii)

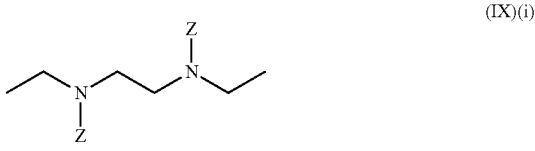
(IX)(i)

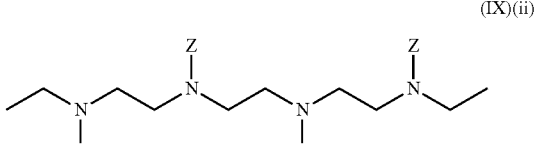
(IX)(ii)

wherein Z represents a hydrogen or a hydrocarbon of $C_1$-$C_{20}$ optionally having unsaturated bonds or hydroxyl groups.

The specific embodiments of the leveler of the present invention are represented in Table 1:

TABLE 1

Specific embodiments of the leveler of the present invention

A. where X is under the general formula (VI)

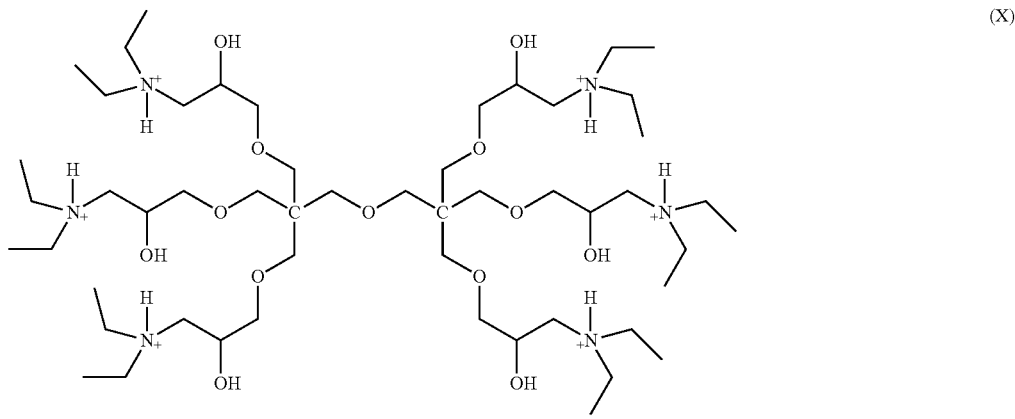

(X)

Compound 1 - where n = 2 (i.e. linker group X represented by formula (VI)(i)) and $R_1$ is represented by formula (III)

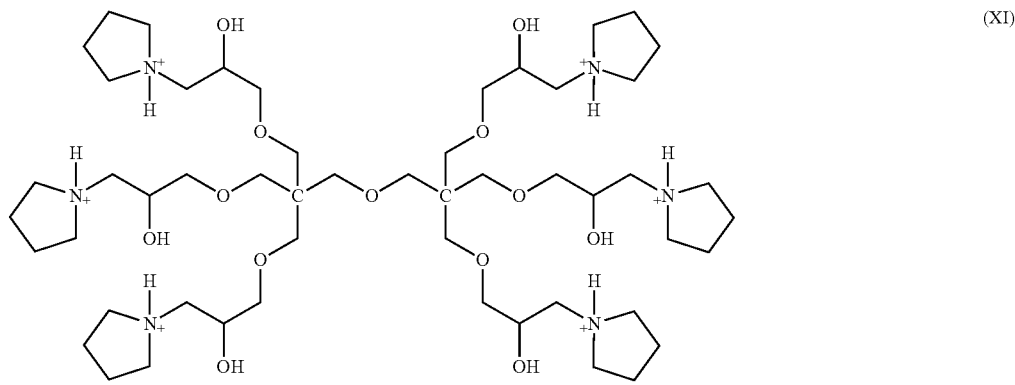

(XI)

Compound 2 - where n = 2 (i.e. linker group X represented by formula (VI)(i)) and $R_1$ is represented by formula (IV)

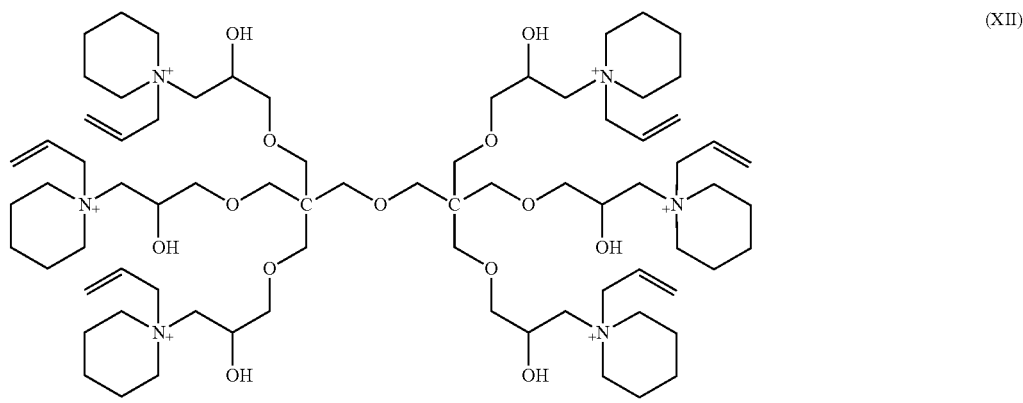

(XII)

Compound 3 - where n = 2 (i.e. linker group X represented by formula (VI)(i)) and $R_1$ is represented by formula (V)

TABLE 1-continued

Specific embodiments of the leveler of the present invention

B. where X is under general formula (VII)

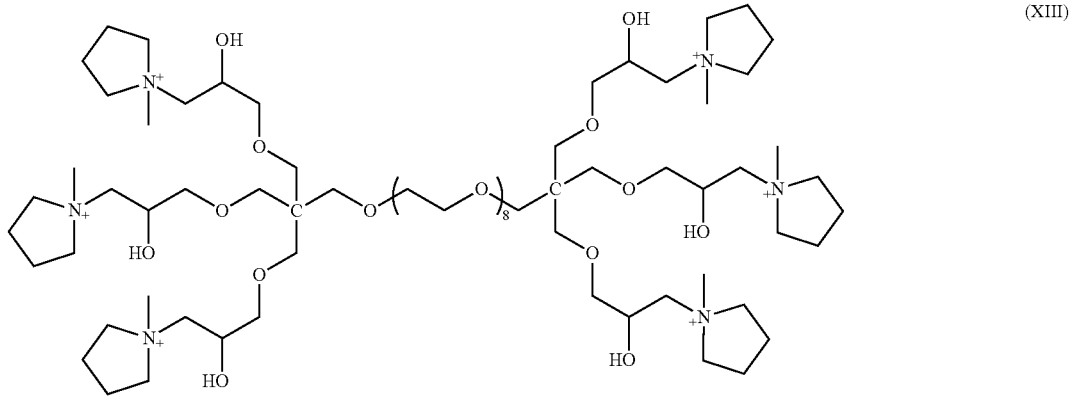

Compound 4 - where n = 8 (i.e. linker group X represented by formula (VII)(i)); Z represents a methyl group; $Z_1$ is a hydrogen; and $R_1$ is represented by formula (IV)

(XIII)

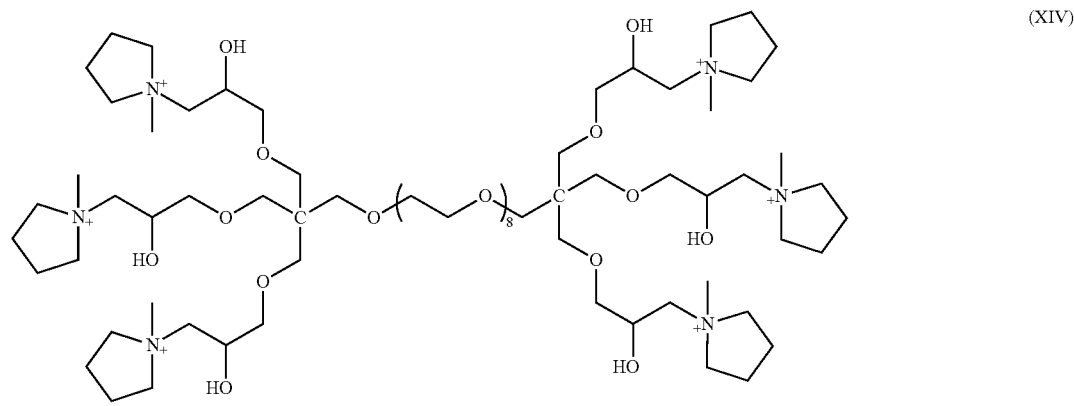

Compound 5 - where n = 8 (i.e. linker group x represented by formula (VII)(ii)); Z represents a methyl group; $Z_1$ is a methyl group; and $R_1$ is represented by formula (IV)

(XIV)

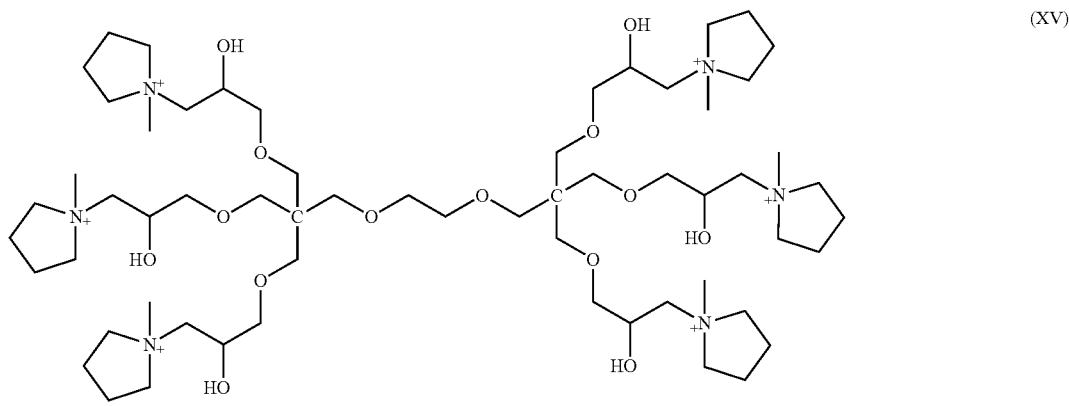

Compound 6 - where n = 1 (i.e. linker group X represented by formula (VII)(iii)); Z represents a methyl group; $Z_1$ is a hydrogen; and $R_1$ is represented by formula (IV)

(XV)

TABLE 1-continued

Specific embodiments of the leveler of the present invention

C. where X is under general formula (VIII)

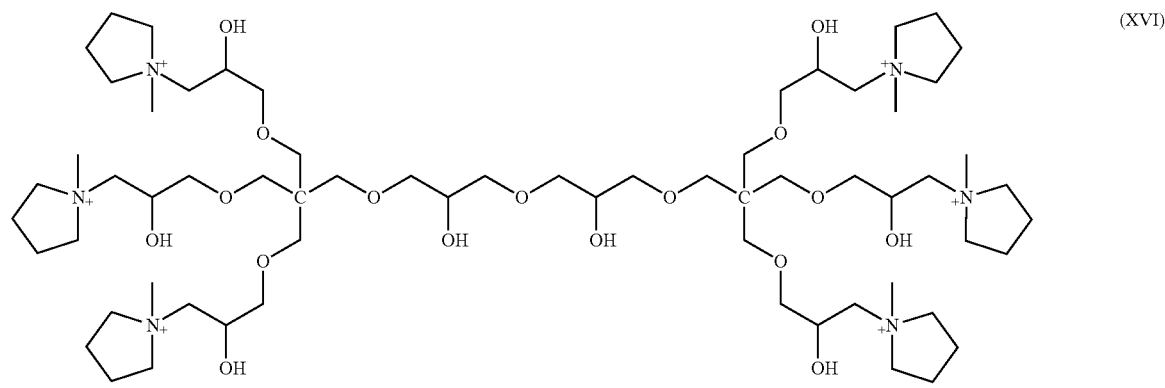

(XVI)

Compound 7 - where n = 2 (i.e. linker group X represented by formula (VIII)(i)); Z represents a methyl group; $Z_2$ is a hydroxyl group; $Z_3$ is a hydrogen; and $R_1$ is represented by formula (IV)

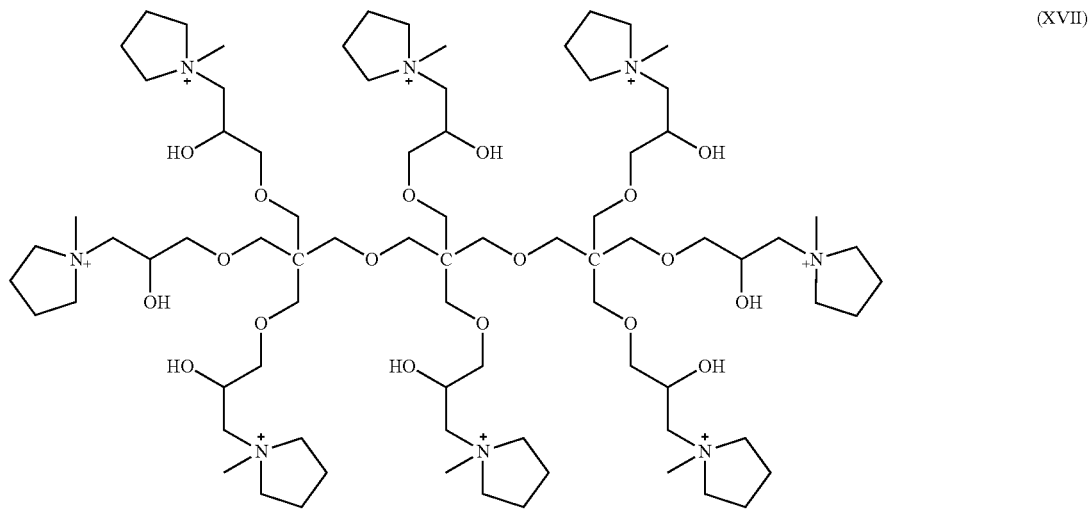

(XVII)

Compound 8 - where n = 2 (i.e. linker group X represented by formula (VIII)(ii)); Z represents a methyl group; $Z_2$ and $Z_3$ are both $R_1$; and $R_1$ is represented by formula (IV)

D. where X is under general formula (IX)

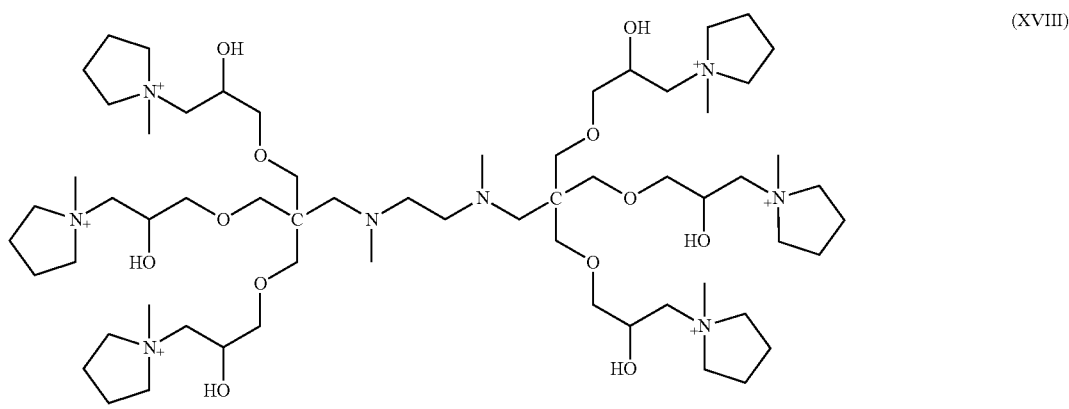

(XVIII)

Compound 9 - where n = 2 (i.e. linker group X represented by formula (IX)(i)); Z and $Z_4$ both represents methyl group; and $R_1$ is represented by formula (IV)

TABLE 1-continued

Specific embodiments of the leveler of the present invention

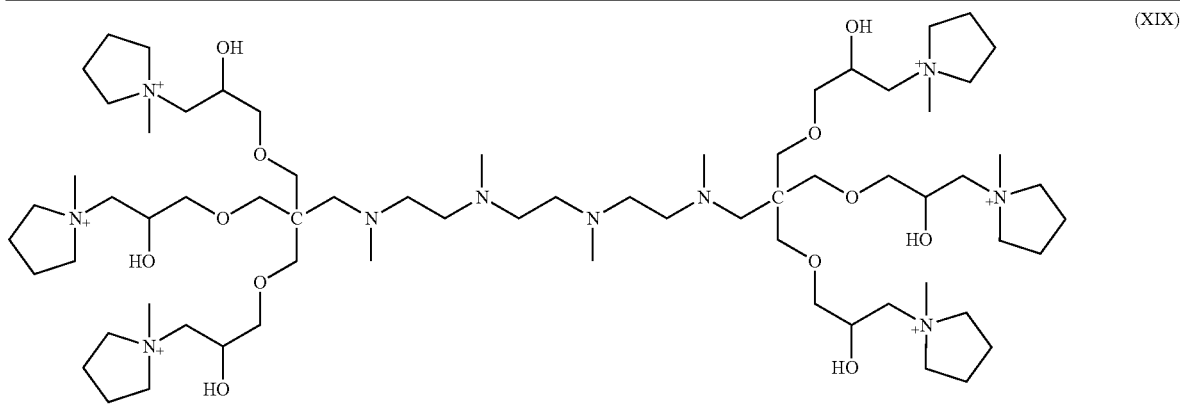

Compound 10 - where n = 4 (i.e. linker group X represented by formula (IX)(i)); Z and $Z_4$ both represents methyl group; and $R_1$ is represented by formula (IV)

Now turning to the method of producing the additive compound/molecule of the present invention, the method comprises the first step of preparing an epoxide-containing reagent by contacting an initiator with an initial reagent (optionally with solvent, base or acid). The epoxide-containing reagent is represented by the following formula (XX)

(XX)

wherein X represents the linker group as mentioned above; and $R_2$ represents a third chained group comprising at least one epoxide. Further, the initial reagent is represented by the following formula (XXI)

(XXI)

wherein X represents the linker group as mentioned above; $R_3$ represents a fourth chained group comprising at least one carbon to carbon double bond or at least one hydroxyl group. The initiator is selected from a group consisting of peroxy acid and a compound represented by the following formula (XXII)

(XXII)

wherein $R_4$ represents a hydrocarbon chain of $C_1$-$C_{20}$; and V represents halogen. In one specific embodiment, the compound represented by formula (XXII) is epichlorohydrin.

The peroxy acid is used to contact (optionally with solvent, base and/or acid) with the initial reagent in which $R_3$ of the initial reagent represents the fourth chained group comprising at least one carbon to carbon double bond to form the epoxide-containing reagent. In one specific embodiment, the peroxy acid is meta-chloroperoxybenzoic acid (m-CPBA).

On the other hand, the compound as represented by formula (XXII) is used to contact (optionally with solvent, base and/or acid) with the initial reagent in which $R_3$ of the initial reagent represents the fourth chained group comprising at least one hydroxyl group to form the epoxide-containing reagent. In one specific embodiment, the compound represented by formula (XXII) is epichlorohydrin.

In the second step, the epoxide-containing reagent is brought into contact with amine (optionally with solvent (which includes alcohol), base and/or acid) to form a tertiary amine compound represented by formula (XXIII)

(XXIII)

wherein X represents the linker group as mentioned above; and $R_5$ represents a fifth chained group comprising a backbone comprising a plurality of carbon atoms and at least one nitrogen moiety. In one embodiment, the at least one nitrogen moiety is in a form of a tertiary amine. In another embodiment, the fifth chained group further comprises a hydroxyl group and at least one carbon atom in the backbone of the fifth chained group is substituted by an oxygen atom. The leveler is then formed by bringing the tertiary amine compound into contact with a halogen-containing reagent (optionally with solvent, base and/or acid) represented by the formula (XXIV)

V—Z (XXIV)

wherein V represents a halogen; and Z is a hydrogen, a hydrocarbon of $C_1$-$C_{20}$ optionally having at least one unsaturated bond or hydroxyl group.

Figure 2:
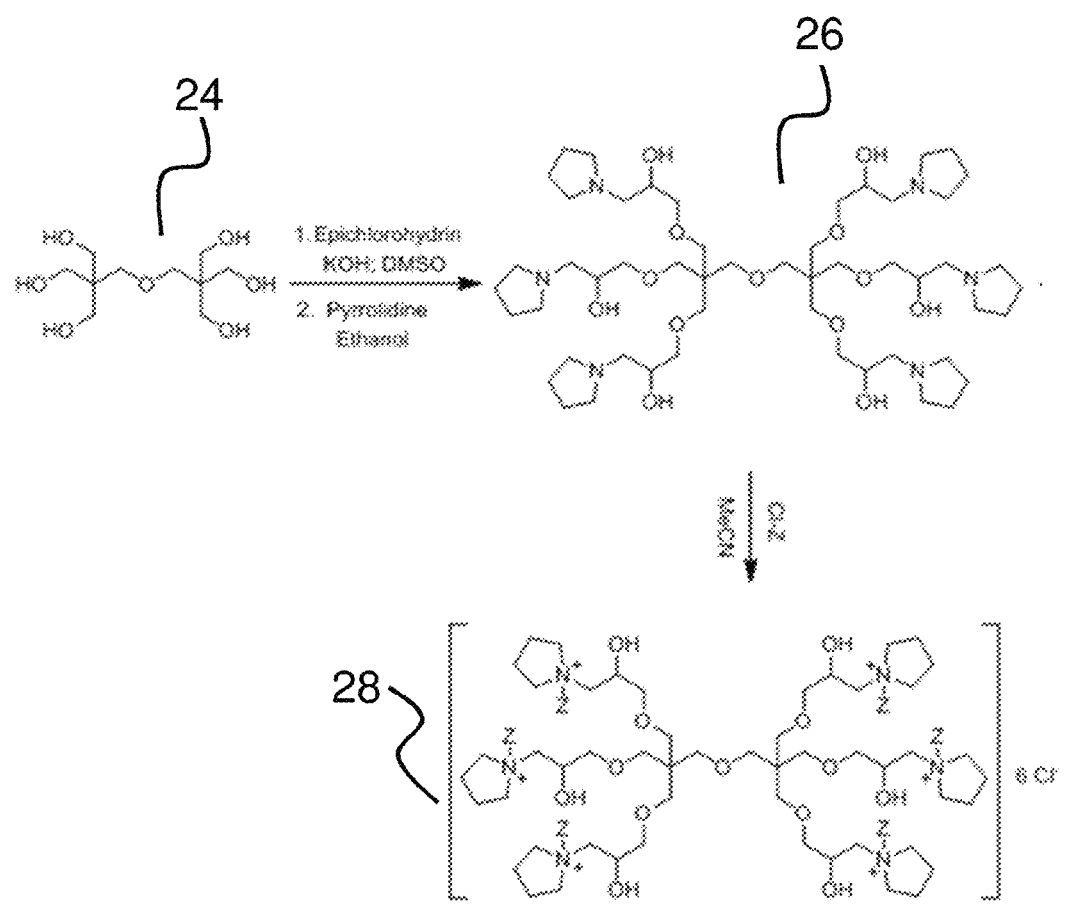
FIG. 2 shows a method of producing the additive compound/molecule according to one specific embodiment of the present invention.

FIG. 2 shows a method of producing the additive compound/molecule 28 according to one specific embodiment of the present invention. As shown in FIG. 2, an initial reagent 24 (i.e. dipentaerythritol or 2,2'-(oxybis(methylene))bis(2-(hydroxymethyl)-propane-1,3-diol) in this specific embodiment) is brought into contact with epichorohydrin in the presence of KOH and dimethyl sulfoxide (DMSO). The epoxide-containing reagent is formed from the above reaction and is further brought into contact with pyrrolidine in the presence of ethanol to form the compound 26. The additive compound/molecule 28 according to one specific embodiment of the present invention is formed by reacting the tertiary amine compound 26 with Cl—Z in the presence of MeCN, wherein Z is hydrogen, a hydrocarbon of $C_1$-$C_{20}$ optionally having at least one unsaturated bond or hydroxyl group.

Figure 3:
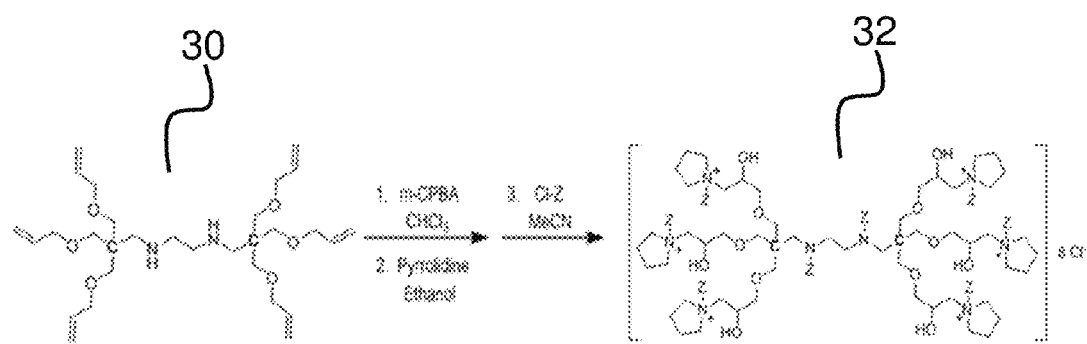
FIG. 3 shows a method of producing the additive compound/molecule according to another specific embodiment of the present invention.
Figure 4A:
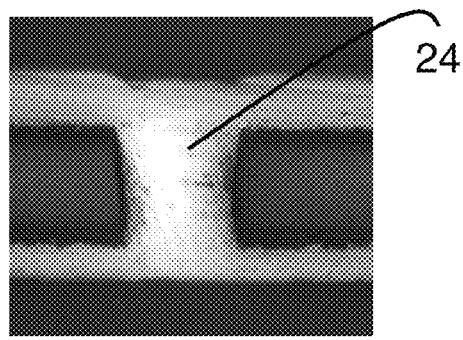
FIG. 4A shows the result of a study of the effect of levelers, which is Compound 1 as represented by formula (X) on electroplating at a predetermined period of time.
Figure 4B:
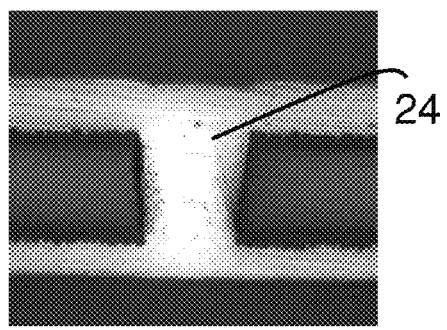
FIG. 4B shows the result of a study of the effect of levelers, which is Compound 3 as represented by formula (XII) on electroplating at a predetermined period of time.
Figure 4C:
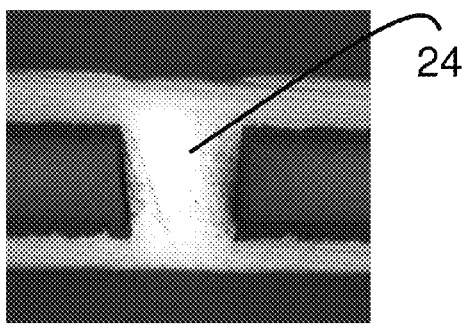
FIG. 4C shows the result of a study of the effect of levelers, which is Compound 5 as represented by formula (XIV) on electroplating at a predetermined period of time.
Figure 4D:
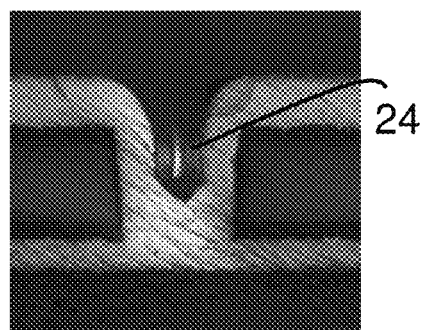
FIG. 4D shows the result of a study of the effect of levelers, which is conventional Janus Green B (JGB) on electroplating at a predetermined period of time.

FIG. 3 shows a method of producing the additive compound/molecule 32 according to another specific embodiment of the present invention. As shown in FIG. 3, an initial reagent 30 is brought into contact with meta-chloroperoxybenzoic acid (m-CPBA) in the presence of $CHCl_3$. The epoxide-containing reagent is formed from the above reaction and further brought into contact with pyrrolidine in the presence of ethanol to form the tertiary amine compound. The additive compound/molecule 32 according to another specific embodiment of the present invention is formed by reacting the tertiary amine compound with Cl—Z in the presence of MeCN, wherein Z is a hydrogen, a hydrocarbon of $C_1$-$C_{20}$ optionally having at least one unsaturated bond or hydroxyl group.

Now turning to a method of electro-deposition of a plating onto a substrate with using the additive compound/molecule of the present invention, in one embodiment, the substrate comprises at least one recess, hole or dimple. In another embodiment, the electro-deposition is an electroplating of copper onto a substrate.

The method of electroplating a substrate with a plating material comprises the steps of firstly preparing an electroplating bath comprising the additive compound/molecule of the present invention as described above and a solution that contains the plating material. In one embodiment, the electroplating bath comprises a suppressor and an accelerator. The non-ionic high molecular polymer is mainly used as suppressor ingredient and the accelerator is a typically low molecular weight sulfur-containing compound, such as bis(sodiumsulfopropyl)disulfide (SPS). In one specific embodiment, the suppressor is selected from the group consisting of PEG, PPG or copolymers thereof. The concentration of the suppressor is between 10 to 2000 mg/L. In another embodiment, the solution that contains the plating material is an acidic copper (II) sulfate (i.e. $CuSO_4$) solution. In one specific embodiment, the concentration of the additive compound/molecule and copper ion in the electroplating bath is between 0.1 to 1000 mg/L and 10 to 80 g/L respectively. In another specific embodiment, the electroplating bath further comprises an organic acid or an inorganic acid at the concentration of 5 to 200 g/L. In yet another embodiment, the electroplating bath further comprises halogen ions and one or more components selected from the group consisting of sulfoalkyl sulfonic acids or salts thereof, bissulfo-organic compounds and dithiocarbamic acid derivatives. The concentration of the halogen ions and the components are 10 to 100 mg/L and 0.1 to 200 mg/L respectively.

After the electroplating bath has been prepared, the substrate is submerged into the electroplating bath. An electric current is then applied to the substrate for a predetermined period of time, for example 60 minutes, such that the plating material is attached onto the surface of the substrate thereby forming a plating on the substrate.

EXAMPLE

The present invention is to be described more specifically with reference to Example. However, materials and, numerical values referred to in the Examples no way restrict the invention and the range of use can of course be changed in accordance with the purpose and the kind of the substrate.

Example 1

Filling Test Comparisons for Blind Via Hole

All the substrates in all the experiments as shown in FIGS. 4A-4D have a hole/recess/dimple 24 of 60 μm in diameter and 50 μm in depth. The electroplating bath comprises:
i. Copper sulfate pentahydrate at a concentration of 220 g/L;
ii. Sulfuric acid (98%) at a concentration of 40 g/L;
iii. Chlorine at a concentration of 40 mg/L;
iv. Bis-(3-sodiumsulfopropyl disulfide) as accelerator at a concentration of 1 mg/L;
v. PEG 6000 as a suppressor at a concentration of 200 mg/L; and
vi. Levelers used in experiments as shown in FIGS. 4A-4D are Compound 1 as represented by formula (X), Compound 3 as represented by formula (XII), and Compound 5 as represented by formula (XIV) and conventional Janus Green B (JGB) respectively. The concentration of all the levelers is 10 mg/L.

Furthermore, the experiments are all carried out at a temperature of 25° C., Ampere per Square Decimeter (ASD) at 1.5 and for 60 minutes. As shown in FIGS. 4A-4D, the filling power of the levelers of the present invention is significantly stronger and better than a conventional leveler. JGB.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:
1. A compound represented by the formula (I)

wherein X represents a linker group comprising a backbone comprising a predetermined number of carbon atoms, in which at least one of the carbon atoms is optionally substituted by oxygen atom and/or nitrogen atom and/or sulfur atom; and $R_1$ represents a positively charged functional group comprising a plurality of carbon atoms and at least one positively charged nitrogen moiety;
wherein $R_1$ is represented by the formula (II)

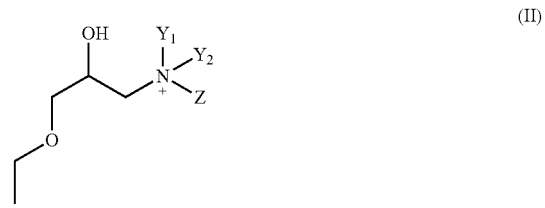

wherein $Y_1$ and $Y_2$ respectively represents a first and second chained group, where each of the chained group comprises a backbone comprising a predetermined number of carbon atoms, wherein at least one of the carbon atoms is optionally substituted by oxygen atoms and/or nitrogen atoms and/or sulfur atoms; and Z represents a hydrogen or a hydrocarbon of C1-C20 optionally having unsaturated bonds or hydroxyl group.

2. The compound of claim 1, wherein the number of carbon atoms in said backbone of said linker group is in a range of 1 and 100 and said backbone comprises at least one unsaturated bond.

3. The compound of claim 1, wherein said predetermined number of carbon atoms in said backbone in each of said first and second chained groups is in a range of 1 and 20.

4. The compound of claim 1, wherein the backbone in each of said first and second chained groups jointly form a cycloalkyl group of $C_3$-$C_8$.

5. The compound of claim 4, wherein $Y_1$ and $Y_2$ further comprises an oxygen atom and/or a sulfur atom.

6. The compound of claim 1, wherein X is selected from a group consisting of the formulas (VI)-(IX):

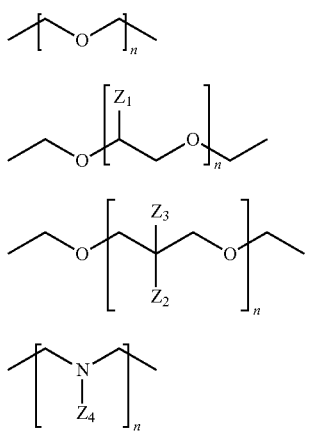

wherein n is in the range of 1 and 50; Z1 represents a hydrogen or hydrocarbon of C1-C20 optionally having at least one unsaturated bond; Z2 represents a hydroxyl group or R1; Z3 represents a hydrogen or R1; and Z4 represents a hydrogen or a hydrocarbon of C1-C20 optionally having unsaturated bonds or hydroxyl groups.

7. A method of electroplating a substrate comprising:
contacting said substrate with an electroplating bath comprising a compound of claim 1 and represented by formula (I); and

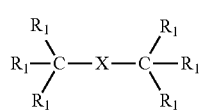

applying an electric current to said substrate for a predetermined period of time such that a plating is formed on said substrate,
wherein X represents a linker group comprising a backbone comprising a predetermined number of carbon atoms, in which at least one of the carbon atoms is optionally substituted by oxygen atom and/or nitrogen atom and/or sulfur atom; and R1 represents a positively charged functional group comprising a plurality of carbon atoms and at least one positively charged nitrogen moiety;

wherein $R_1$ is represented by the formula (II)

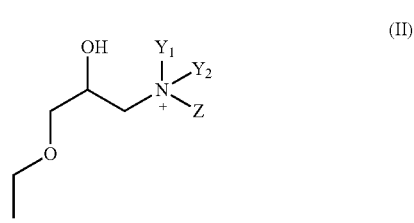

wherein $Y_1$ and $Y_2$ respectively represents a first and second chained group, where each of the chained group comprises a backbone comprising a predetermined number of carbon atoms, wherein at least one of the carbon atoms is optionally substituted by oxygen atoms and/or nitrogen atoms and/or sulfur atoms; and Z represents a hydrogen or a hydrocarbon of C1-C20 optionally having unsaturated bonds or hydroxyl group.

8. The method of claim 7, wherein the concentration of said compound in said electroplating bath is between 0.1 to 1000 mg/L.

9. The method of claim 7, wherein said electroplating bath further comprises copper ions and said plating formed on said substrate is substantially copper, wherein the concentration of said copper ions in said electroplating bath is between 10 to 80 g/L.

10. The method of claim 7, wherein said electroplating bath further comprises an organic acid or an inorganic acid at the concentration of 5 to 200 g/L.

11. The method of claim 7, wherein said electroplating bath further comprises halogen ions and the concentration of said halogen ion is between 10 to 100 mg/L.

12. The method of claim 7, wherein said electroplating bath further comprises one or more components selected from the group consisting of sulfoalkyl sulfonic acids or salts thereof, bissulfo-organic compounds and dithiocarbamic acid derivatives and the concentration of said components is between 0.1 to 200 mg/L.

13. The method of claim 7, wherein said electroplating bath further comprises a suppressor selected from the group consisting of PEG, PPG or copolymers thereof and the concentration of said suppressor is between 10 to 2000 mg/L.

* * * * *